(12) United States Patent
Esplin

(10) Patent No.: US 6,712,830 B2
(45) Date of Patent: Mar. 30, 2004

(54) SOFT TISSUE ANCHOR

(75) Inventor: Vermon S. Esplin, Pocatello, ID (US)

(73) Assignee: Esplin Medical Inventions, L.L.C., Mountain Green, UT (US)

( * ) Notice: Subject to any disclaimer, the term of this patent is extended or adjusted under 35 U.S.C. 154(b) by 88 days.

(21) Appl. No.: 09/808,456

(22) Filed: Mar. 14, 2001

(65) Prior Publication Data

US 2001/0051815 A1 Dec. 13, 2001

Related U.S. Application Data

(60) Provisional application No. 60/189,554, filed on Mar. 15, 2000.

(51) Int. Cl.$^7$ ................................................. A61B 17/04
(52) U.S. Cl. ...................................................... 606/152
(58) Field of Search ................................. 606/152, 216

(56) References Cited

U.S. PATENT DOCUMENTS

| | | | | |
|---|---|---|---|---|
| 268,632 A | * | 12/1882 | Danforth ..................... | 24/380 |
| 4,469,101 A | | 9/1984 | Coleman et al. ......... | 128/334 R |
| 4,971,075 A | | 11/1990 | Lee ............................. | 128/898 |
| 5,061,283 A | | 10/1991 | Silvestrini ................... | 623/13 |
| 5,263,973 A | * | 11/1993 | Cook .......................... | 606/215 |
| 5,290,217 A | | 3/1994 | Campos ...................... | 600/37 |
| 5,425,766 A | | 6/1995 | Bowald ....................... | 623/13 |
| 5,458,636 A | | 10/1995 | Brancato ..................... | 623/11 |
| 5,697,933 A | | 12/1997 | Gundlapalli et al. ......... | 606/96 |
| 5,800,544 A | | 9/1998 | Demopulos et al. .......... | 623/13 |
| 5,916,224 A | | 6/1999 | Esplin ......................... | 606/151 |
| 5,931,840 A | | 8/1999 | Goble et al. .................. | 606/73 |
| 5,961,520 A | | 10/1999 | Beck, Jr. et al. .............. | 606/72 |

* cited by examiner

*Primary Examiner*—Gary Jackson
(74) *Attorney, Agent, or Firm*—Pate Pierce & Baird

(57) ABSTRACT

An apparatus and method for repairing severed or unattached soft tissue of the body, such as tendons, typically includes an anchor for engaging the soft tissue and a securement mechanism designed to securely attach the anchor to the soft tissue and to abut the soft tissue against a surface. The surface may be second soft tissue, a bone, or the like. The anchor may be formed as a plate and may include a plurality of apertures formed therein. Selected apertures of the plurality of apertures formed in the anchor may be configured to receive sutures therethrough. Other apertures of the plurality of apertures formed in the anchor may be configured to permit synovial fluid to contact the soft tissue below the anchor. The anchor may also include a plurality of teeth extending generally away from one surface of the anchor in a transverse direction and configured to penetrate soft tissue. Such teeth are typically configured to substantially restrict longitudinal movement between the anchor and the soft tissue. A soft tissue repair may also include a second anchor to be secured to a second soft tissue for abutting the second soft tissue substantially against the soft tissue secured by the first anchor.

20 Claims, 15 Drawing Sheets

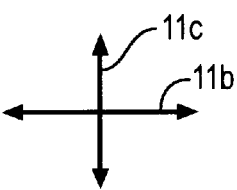
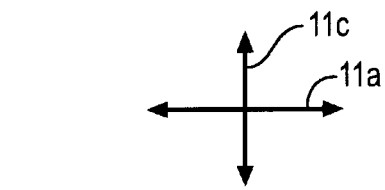
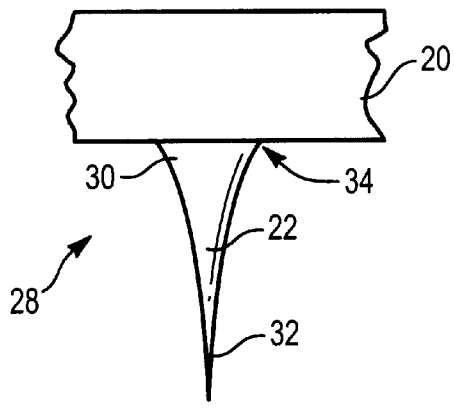
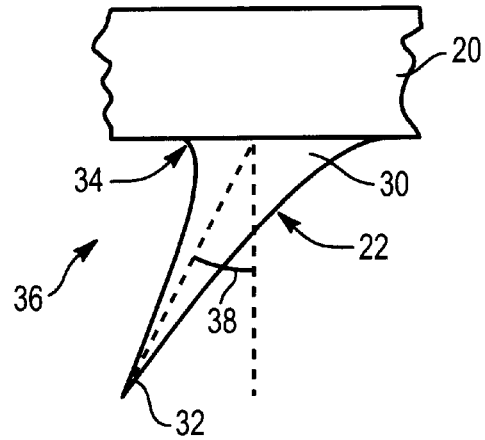
FIG. 4a  FIG. 4b
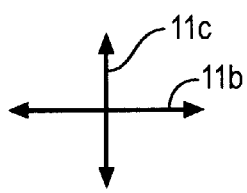
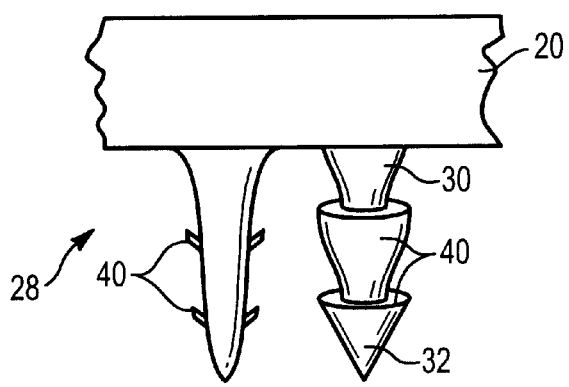
FIG. 5

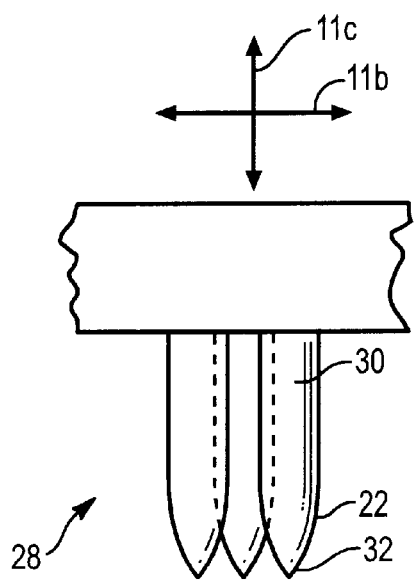
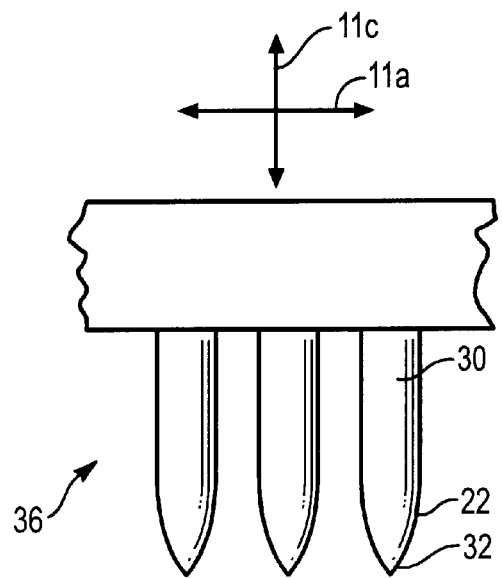
FIG. 7a  FIG. 7b
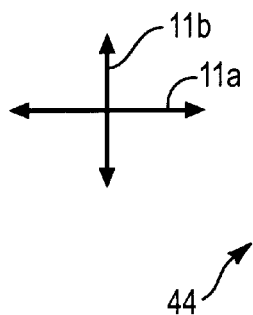
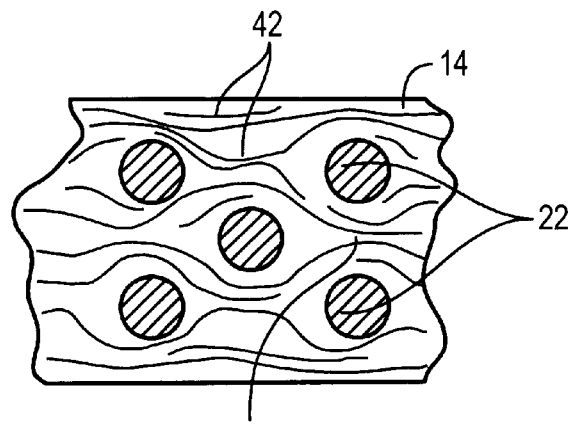
FIG. 7c

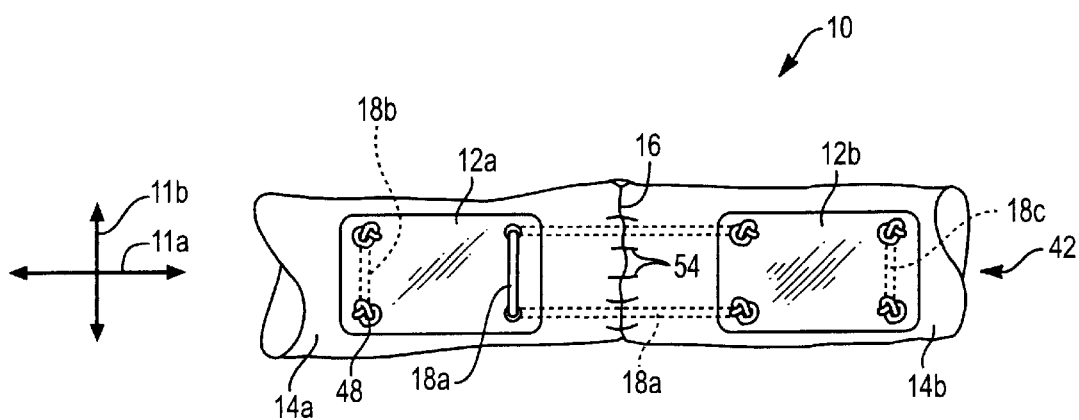
FIG. 13a
FIG. 13b
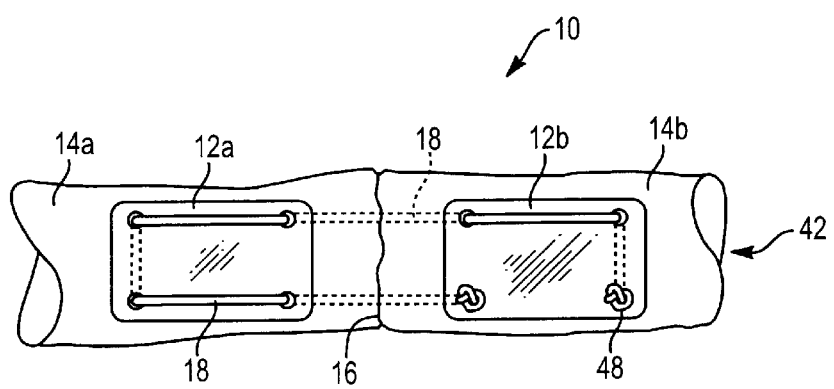
FIG. 14a
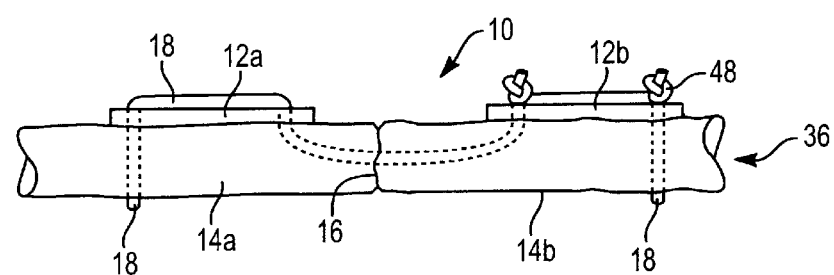
FIG. 14b

SOFT TISSUE ANCHOR

RELATED APPLICATIONS

This application is a continuation of a U.S. Provisional Application, Ser. No. 60/189,554, filed on Mar. 15, 2000 and directed to a Soft Tissue Grip.

BACKGROUND

1. Field of the Invention

This invention relates to medical devices and, more particularly to novel apparatus and methods for soft tissue repair.

2. Background

Soft tissue of the human body, and more particularly the tendons of the hands and feet, are occasionally exposed to laceration and rupture. Repair of lacerated or ruptured tendons or other soft tissues is often complicated. Unless immobilized, tendons and other soft tissues of the body are typically under tensile loads of one amount or another. Such tensile loads on tendons tend to complicate the repair of tendons and other soft tissues. Tendons also tend to heal slowly. Tendons often receive a very limited supply of blood. It has been found that tendons receive most of their nutrition by diffusion via the synovial fluid. The diffusion process is slow and does not promote rapid healing of damaged tendon tissue. Furthermore, research has shown that tendons heal with a higher tensile strength and improved gliding ability when they are mobilized early and often during the healing process. When tendons are mobilized, however, they are exposed to tensile loads, which may rupture a repair made using current techniques.

An effective soft tissue repair must, therefore, simultaneously hold the severed ends together, support the tensile loads that are required for mobilization, and allow the nutrient fluid access to the soft tissue to provide the nutrition needed for healing.

Current suture methods have been found lacking. If a suture of sufficient strength to support the tensile loads of mobilization is used, the suture typically pulls through the soft tissue. If a thinner suture is used to prevent tear through, the suture itself is often unable to support the tensile loads associated with mobilization.

Tendon clips have been introduced to grip the tendon ends and hold them together. Tendons clips have several drawbacks. They are typically circumferential devices and significantly restrict the flow of nutrients to the tendon cells, possibly causing necrosis of the tendon. As the tendon negotiates around pulleys and corners and through synovial sheaths, the tendon clip may cut into the fibers of the tendon. The typical tube shape tendon clips make a relatively inflexible restraint to the naturally flexible tendon, again increasing the likelihood of damaging the tendon. The circumferential nature increases the bulk of the device, limiting the possible areas of application. Furthermore, tendon clips require multiple sizes, thus increasing manufacture costs and increasing the time consumed in finding the best fit.

Some current tendon clips require crimping, creating the possibility of crushing or otherwise damaging the tendon. Additionally, crimping requires special pliers, which, in many instances, may not be admitted into the confined spaces where tendons frequently are injured.

Current tendon grafting methods have also been found lacking. Grafts are often required when an injury has destroyed a significant length of tendon. In many cases, a graft can not be installed immediately upon need. Typically, a synthetic rod is placed in the location where the graft is needed. The rod maintains the spacing and passageway while the surrounding tissue heals. After the surrounding environment has healed, a surgeon removes the rod and inserts the graft. This process requires two surgeries, greatly increasing the cost of the procedure. Additionally, the patient is without the use of his/her full physical capabilities for six to eight weeks per surgery. A simple grafting procedure is needed which will allow the graft to be completed in a single surgery, thus reducing costs and patient down time.

In view of the foregoing, it would be an advancement in the art to produce an apparatus and method for securing a soft tissue repair site while simultaneously preventing tear through, allowing for early and relatively complete mobilization of the joints associated with the repaired tissue, and minimizing the soft tissue area that can not be accessed by the nutrient fluids. Such an apparatus would minimize the need for expensive splints and costly occupational therapy used to mobilize repaired soft tissues without exceeding the limited forces supported by current repairs methods.

BRIEF SUMMARY AND OBJECTS OF THE INVENTION

In view of the foregoing, it is a principal object of the present invention to provide a soft tissue repair of sufficient strength to allow an immediate and active mobilization of the soft tissue.

It is also an object of the present invention to provide a repair that will allow smooth motion of the repaired soft tissue through tight anatomical passageways.

It is a further object of the present invention to provide a repair that will maximize the surface area of the soft tissue that may be exposed to nutrient fluids that aid in the healing process.

It is another object of the present invention to provide a repair sufficiently flexible to allow the repair site to bend and move as it passes around pulleys and other structures within the body.

It is another object of the present invention to provide a repair that may be easily implemented by a variety of medical specialties, including without limitation general orthopaedists, plastic surgeons, and hand surgeons.

The foregoing objects and benefits of the present invention will become clearer through an examination of the drawings, description of the drawings, description of embodiments, and claims which follow.

Consistent with the foregoing objects, and in accordance with the invention as embodied and broadly described herein, an apparatus and method are disclosed, in suitable detail to enable one of ordinary skill in the art to make and use the invention.

In certain embodiments an apparatus and method in accordance with the present invention may include an anchor configured to engage soft tissue of the body. The anchor may comprise a plate formed to have longitudinal, lateral, and transverse directions substantially orthogonal to one another. The plate may have a plurality of apertures and a top and a bottom surface defined by the transverse direction. Selected apertures of the plurality of apertures may be configured to receive sutures therethrough. Other apertures of the plurality of apertures may provide access for a nutritional fluid, such as synovial fluid, to the soft tissue.

In selected embodiments, a plurality of teeth may extend generally transversely from the bottom surface of the plate.

The teeth may penetrate the soft tissue to substantially prevent longitudinal motion between the anchor and the soft tissue. The number and geometry of the teeth may be selected to provide strength of engagement of the anchor to the soft tissue while minimizing the risk of tearing and injury to the soft tissue.

A securement mechanism may transversely secure the anchor to the soft tissue. The securement mechanism may be a circumferential band, a suture, or any other suitable mechanism capable of transversely securing the anchor to the soft tissue without covering significant portions of the soft tissue surface. In one presently preferred embodiment, the securement mechanism comprises a suture secured to the plate, passing transversely through the soft tissue, passing over some distance on the surface of the soft tissue, reentering the soft tissue to pass transversely therethrough, and securing again to the anchor.

In certain embodiments, the suture may make several passes transversely through the soft tissue. The number of passes may be selected to provide both transverse and longitudinal securement of the anchor to the soft tissue, thus eliminating the need for the plurality of teeth.

When the anchor is properly transversely and longitudinally secured to the soft tissue, the anchor provides a "handle" on the soft tissue. The "handle" enables a surgeon to position the severed end or surface of the soft tissue against any desired surface. The anchor distributes whatever loads are applied to it over a relatively large area of the soft tissue. Such distribution of loads prevents any particular point or location in the soft tissue from supporting all, or significant portions, of the applied loads. Thus, the anchor may greatly reduce the risk of tearing of the soft tissue and subsequent repair failure even while supporting significant mobilization loads.

The opposing surface to which the soft tissue may be abutted may be a similar or dissimilar tissue. In selected embodiments, the soft tissue may be a first severed tendon. The first severed tendon end may be abutted against a second tendon having a similarly severed end. In such a situation, it is typically desirable to provide at least one anchor to engage both tendons. A longitudinal connector may connect at least one anchor on the first tendon to at least one anchor on the second tendon. The longitudinal connector, in cooperation with the anchors, abuts the severed surfaces of the first and second tendons creating a repair site. Additionally, the longitudinal connector supports whatever tensile loads of mobilization may be applied across the repair site, thus preventing the repair site from being pulled apart while the soft tissue heals. Several stitches may be incorporated at the repair site to aid the repair in maintaining a proper alignment.

In certain embodiments, the soft tissue may again be a first severed tendon. The severed first end may be abutted against a first end of a graft tendon segment. A second severed tendon end may be abutted against the second end of the graft tendon. At least one anchor may engage the first severed tendon end and at least one anchor may engage the second severed tendon end. A longitudinal securement mechanism may extend from an anchor secured to the first severed tendon to an anchor secured to the second severed tendon end. The longitudinal securement mechanism may extend alongside or through the graft tendon segment. In such a configuration, the repair in accordance with the present invention provides a method of securing both repair sites (both ends of the graft) with a single repair.

If the graft segment is comparatively long, it may desirable to provide a repair for each end of the graft. In such a configuration, longitudinal securement mechanisms may simply extend from an anchor secured to the first severed tendon end to an anchor secured to the first end of the graft segment. A similar longitudinal securement mechanism may be provided for the other end of the graft.

In other embodiments in accordance with the present invention, the repair may abut a soft tissue, such as a tendon, against a dissimilar tissue, such as a bone. In such a configuration, at least one anchor may engage a first tendon end. A longitudinal securement mechanism may engage an anchor secured to the tendon and extend to a tie-off region. The tie-off region may provide a stop to which the longitudinal securement mechanism may be secured to maintain the tendon end against the bone.

The longitudinal securement may be any suitable mechanism that provides the proper balance of tensile strength and flexibility. The proper balance may vary from repair to repair. The longitudinal securement mechanism must also allow for securement to the anchors. In one embodiment, the longitudinal securement mechanism may be a suture of a size selected to provide the necessary tensile strength.

BRIEF DESCRIPTION OF SEVERAL VIEWS OF THE DRAWING

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIGS. 4a and 4b depict front and side elevation views of a tooth in accordance with the present invention;

FIG. 5 is a side elevation of an alternative embodiment of a tooth in accordance with the present invention;

FIGS. 7a, 7b, and 7c depict front elevation, side elevation, and top cross sectional views of an embodiment of teeth positioning in accordance with the present invention;

FIGS. 13a and 13b depict top and side views of an embodiment of a repair in accordance with the present invention;

FIGS. 14a and 14b depict top and side views of an alternative embodiment of a repair in accordance with the present invention;

DETAILED DESCRIPTION OF THE INVENTION

It will be readily understood that the components of the present invention, as generally described and illustrated in the Figures herein, may be arranged and designed in a wide variety of different configurations. Thus, the following more detailed description of the embodiments of the system and method of the present invention, as represented in FIGS. 1 through 22, is no t intended to limit the scope of the invention.

Those of ordinary skill in the art will, of course, appreciate that various modifications to the details of the Figures may easily be made without departing from the essential characteristics of the invention. Thus, the following description of the Figures is intended only as an example, and simply illustrates one presently preferred embodiment that is consistent with the invention.

Figure 1:
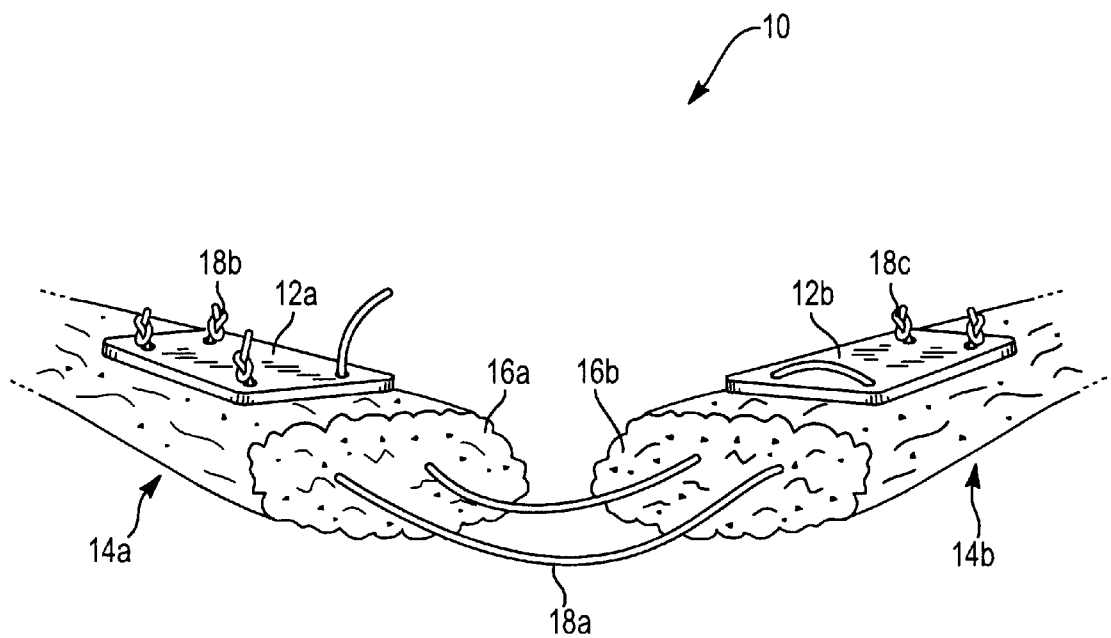
FIG. 1 is a perspective view of a tendon repair in accordance with the present invention.

FIG. 1 illustrates a repair 10 in accordance with the present invention. A plurality of anchors 12a, 12b is shown engaging a soft tissue 14, which has been severed into left soft tissue 14a and a right soft tissue 14b. A repair site 16 may be defined as a left repair surface 16a and a right repair surface 16b. The anchors 12 may be spaced any suitable distance from the repair site 16. A transverse securement mechanism 18b may transversely secure the anchors 12 to the soft tissue 14. A longitudinal securement mechanism 18a may engage the anchors 12a, 12b and be pulled tight to draw the repair surfaces 16a, 16b together. The natural healing process of a body corresponding to the damaged soft tissue may then regenerate the cells necessary for joining the soft tissues 14a and 14b to form whole, operable soft tissue unit 14.

The soft tissue 14 illustrated depicts a flexor tendon. A repair 10 in accordance with the present invention, however, may be applied to a variety of lacerations and ruptures throughout the human body, or bodies of selected animals. The repair 10 may be applied to the wrist, forearm, leg, ankle, achilles tendon, rotator cuff, patella, quadriceps tendon, hands, and feet. The repair may be particularly applicable to fibrous soft tissue 14 that supports tensile loads. Additionally, the repair 10 need not be limited to securing soft tissue to itself. The repair 10 may secure a tendon or the like to a bone or other dissimilar structure. Hereinbelow, the term tendon will be used to refer to the group of soft tissues 14 and fibrous tissues 14 to which the repair 10 in accordance with the present invention may be applied.

The securement mechanism 18 may be a suture 18 made of a metal, a polymer, a bio-absorbable, or any other suitable material. Sutures 18 typically are manufactured in a variety of thicknesses and strengths. The nature of the repair 10 may dictate the suture that may be most suitable. Hereinbelow, the term suture 18 will be used to refer to the group of securement mechanisms that may be employed in a repair 10 in accordance with the present invention.

Figure 2:
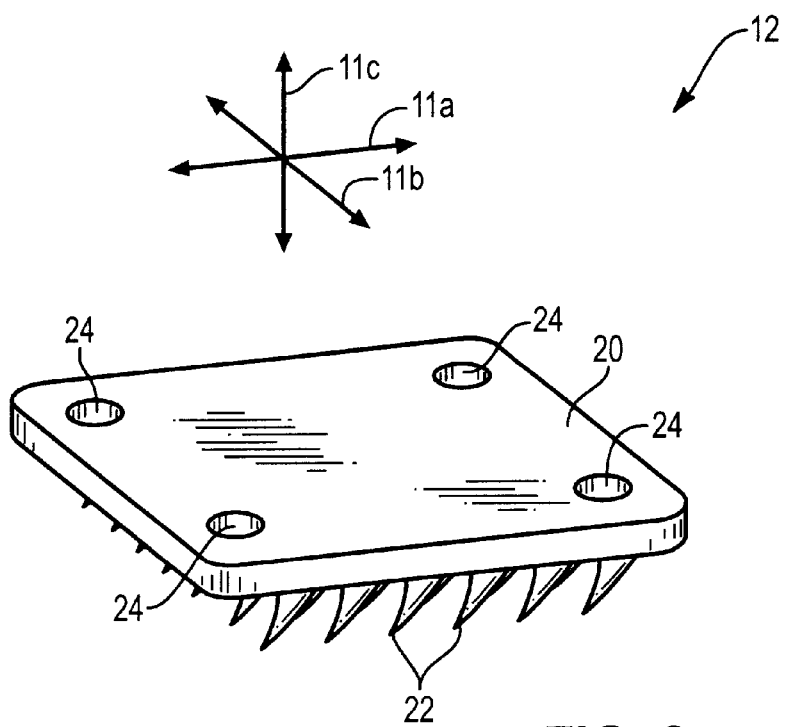
FIG. 2 is a perspective view of an embodiment of a soft tissue anchor.

FIG. 2 is a perspective view of an embodiment of a soft tissue anchor 12. A coordinate axis of longitudinal 11a, lateral 11b, and transverse 11c directions, substantially orthogonal to one another, may be defined. The anchor 12 may comprise a substantially rectangular plate 20. Teeth 22 may extend substantially transversely from the underside of the plate 20. The plate 20 may include a plurality of apertures 24 to allow for a suture 18 to engage the anchor 12.

Current medical standards typically require that implants, such as the anchor 12, have a unitary construction. The unitary construction prevents the implant from separating into subunits which may disseminate and cause injury. The anchor 12 may be made of medical grade stainless steel, titanium, a polymer, a carbon reinforced polymer, a bio-absorbable material, or any other suitable material. The anchor 12 may be machined from a single piece of stock. Alternatively, the anchor 12 may be formed in a molding process.

In certain embodiments, the anchor 12 may be a single unit machined from titanium. The titanium allows for an anchor 12 that may be very small while still possessing the necessary strength. In an alternative embodiment, the anchor 12 may be molded of a flexible polymer to allow for the plate 20 to flex and follow the bending and motion of the soft tissue 14. Additionally, the anchor 12 may be formed of a bio-absorbable material to provide a repair 10 that need not be removed after the healing is completed.

The teeth 22 may be of any suitable length. The length of the teeth may be selected to enable secure engagement of the tendon 14 without causing unnecessary damage to the tissue 14. It may be desirable to select a tooth length that will cause allow the teeth 22 to completely pass through the cross section of the tendon 14. The number of teeth 22 incorporated into the anchor 12 may be selected to balance gripping ability of the anchor 12 against damage to the tendon 14 and manufacturability of the anchor 12.

The teeth 22 may be of any suitable width. The width may be selected to resist the shear applied by the longitudinal 11a tensile loads acting on the anchor 12. If the anchor is to be constructed of a bio-absorbable material, the width of the teeth 22 may be modified to provide the required strength for the required healing time. Some soft tissues 14, such as tendons 14, have relatively little fluid flow therethrough, thus, causing the teeth 22 to be absorbed at a relatively slow rate. In such a case, the width of the teeth 22 need be modified only slightly to provide the necessary life span for the repair 10.

Figure 3:
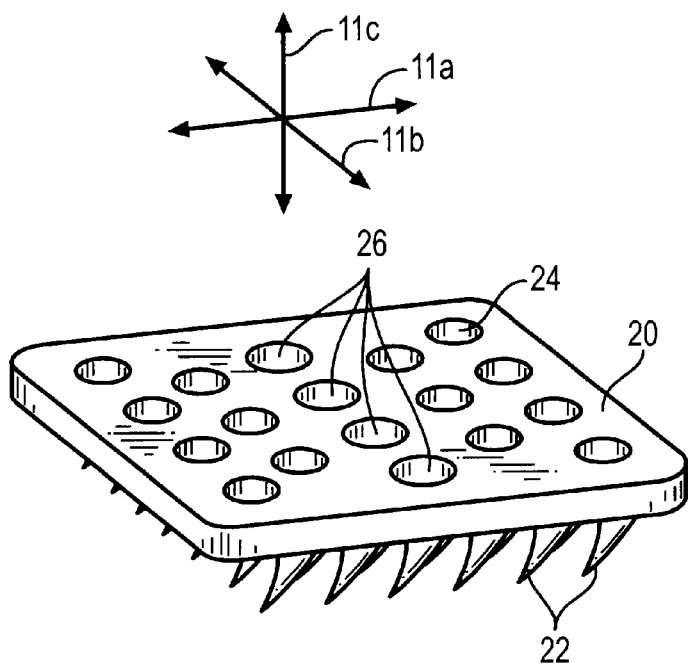
FIG. 3 is a perspective view of an alternative embodiment of a soft tissue anchor.

Referring to FIG. 3, tendons 14 typically glide within synovial sheaths. The sheaths often contain synovial fluid. Synovial fluid lubricates the tendons 14, promoting a smooth glide between the tendons 14 and the sheaths. The synovial fluid is also the primary source of nutrition for the fibrocyte cells of the tendon 14.

In one embodiment, the anchor 12 may have apertures 26 extending transversely 11c through the plate 20. The apertures 26 may allow synovial fluid to reach the tendon 14, thus preventing necrosis of the tendon while speeding the healing process.

Referring to FIGS. 4a and 4b, various configurations of a tooth 22 may be implemented in the design of the anchor 12. A front elevation view 28 illustrates one presently preferred geometry of a tooth 22. The tooth 22 may include a base 30 tapering down to a sharp tip 32. At the base 30, the tooth 22 may have a radius 34 to provide strength to the tooth 22 and prevent separation of the tooth 22 from the plate 20.

As illustrated in side elevation 36, the tooth 22 may have a forward angle 38. The angle 38 tilts the tooth 22 in a longitudinal direction 11a. The angle 38 may vary depending on tooth 22 material, given the expected longitudinal 11a forces the tooth 22 must resist. The angle 38 may be selected to promote engagement of the tendon 14 as the anchor is pulled in a longitudinal direction 11a corresponding to the angle 38.

In certain embodiments, the base 30 may be wider in the longitudinal direction 11a. The added width strengthens the tooth 22 against forces in a longitudinal direction 11a. The anchor 12 may then be aligned so that the greatest forces act in a longitudinal direction 11a. The tooth 22 may have a smooth oval cross section, thus eliminating sharp edges that may tend to cut and weaken the tendon 14. In such a configuration, the tooth 22 may be relatively strong without unnecessarily damaging the tendon 14.

Referring to FIG. 5, in selected embodiments, a tooth 22 that includes structure configured to resist extraction in a transverse direction 11c from the tendon 14 may be advantageous. In one embodiment, the teeth 22 may include a plurality of barbs 40. A barb 40 may be a individual finger extending from the tooth 22. In an alternative embodiment, the barb 40 may comprise an abrupt decrease in tooth 22 diameter/width.

Figure 6:
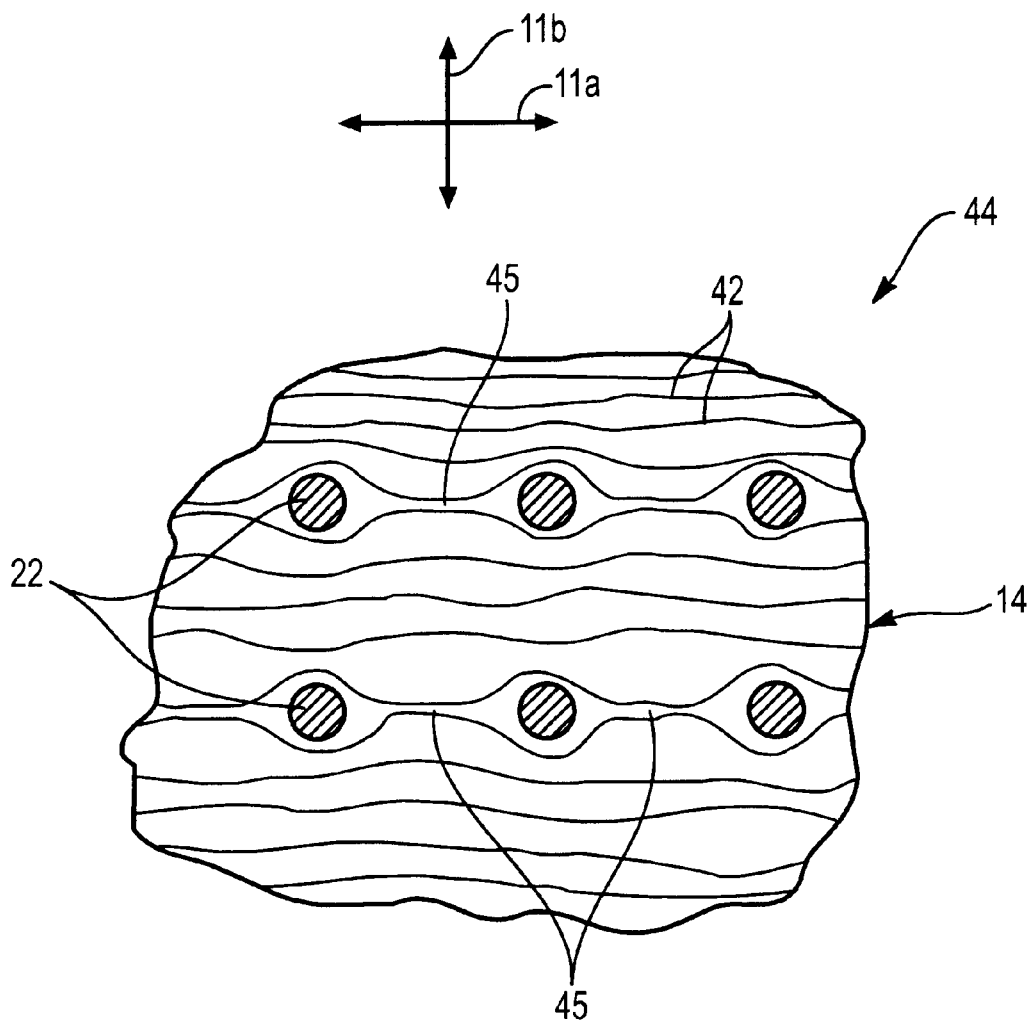
FIG. 6 is a top cross sectional view of an alternative embodiment of teeth positioning in accordance with the present invention.

Referring to FIGS. 6 and 7, as discussed hereinabove, selected embodiments in accordance with the present invention may be configured for use with fibrous soft tissue 14. Often, fibrous tissue 14 comprises many fibers 42 running in a common direction 11a. Such a configuration of fibers 42 promotes tensile strength in the aligned direction 11a, but also facilitates splitting and lateral 11b separation of the tissue.

FIG. 6 illustrates atop cross sectional view 44 of an embodiment of teeth 22 corresponding to an anchor 12 used for a repair 10. The teeth 22 are aligned longitudinally 11a. The alignment of the teeth 22 creates an alignment of a plurality of weakened regions 45. As the tissue 14 is loaded in tension along the longitudinal axis 11a, the weakened regions 45 experience a separating force in a lateral direction 11b. If the separating force becomes excessive, the weakened regions 45 will separate, the anchor 12 will tear through the tissue 14, and the repair will fail. In selected tissues 14, the force needed to separate the weakened regions 45 may be great enough that little or no risk of tear through exists with respect to a repair 10. In other tissues 14, however, it may be desirable to reposition the teeth 22 to mitigate the risk of tearing through the tissue 14.

FIGS. 7a, 7b, and 7c, illustrate one embodiment of teeth 22 positioned to mitigate the risk of tearing through tissue 14. As best shown in FIG. 7c, the teeth 22 may be aligned in a manner to engage the fibers 44 of the tendon 14 in a weaving pattern. The teeth 22 may be alternatingly staggered and/or angled in a lateral direction 11b. As the teeth 22 penetrate the tendon 14, the fibers 44 are spaced laterally 11b by the diameter/width of the teeth 22. As the tissue 14 is loaded in tension along the longitudinal axis 11a, the weakened regions 45 will again experience a separating force in a lateral direction 11b. The weakened regions 45, however, may not have to bear the separating force alone. In the staggered arrangement, a tooth 22 may be located on each side of the weakened region 45. The teeth 22, in the staggered arrangement, support and resist the lateral 11b separating force, thus preventing separation and greatly reducing the risk of tearing through tissue 14.

Figure 8:
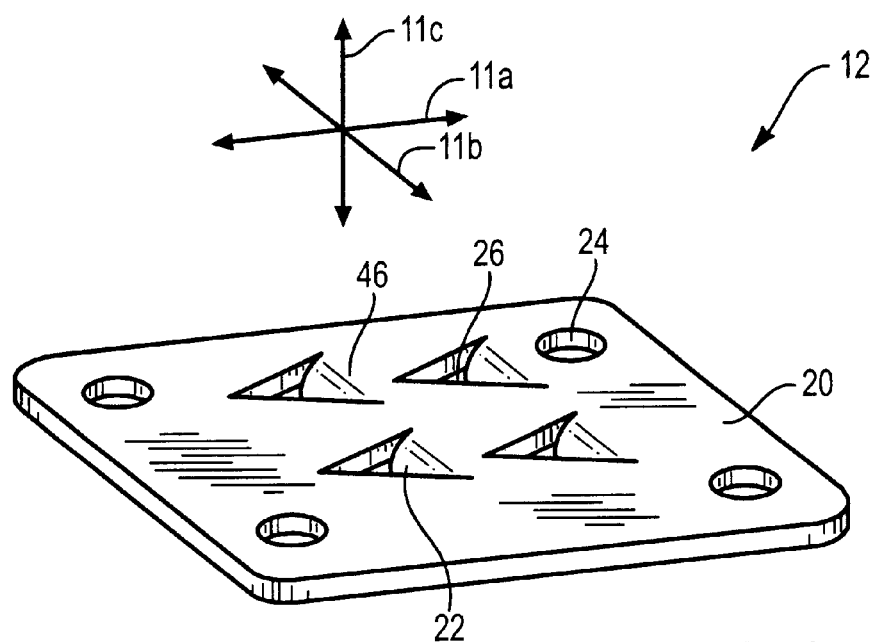
FIG. 8 is a perspective view of an alternative embodiment of a anchor in accordance with the present invention.
Figure 9:
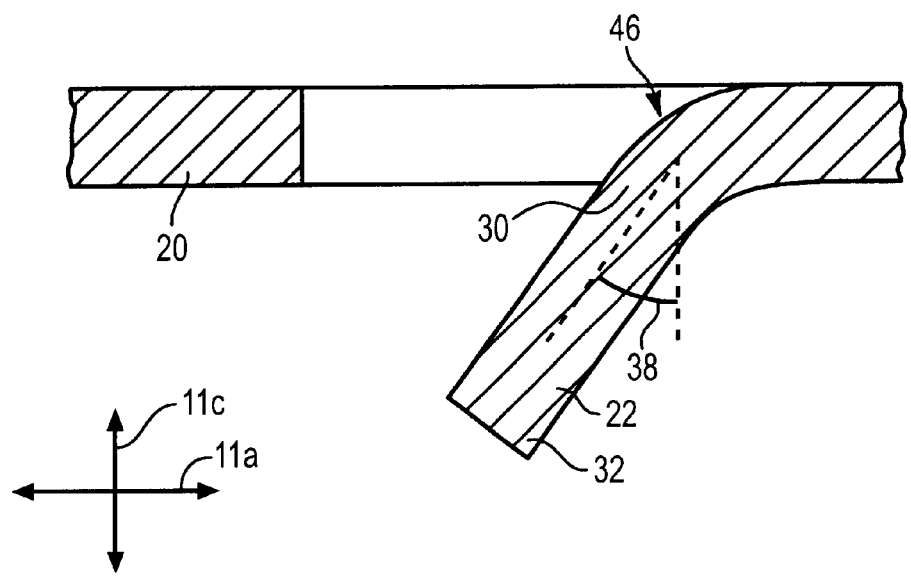
FIG. 9 is a cross sectional view of an embodiment of a tooth corresponding to the embodiment of the anchor of FIG. 8.

Referring to FIGS. 8 and 9, in certain embodiments, it may be advantageous to design an anchor 12 that may be stamped out of a single piece of metal. The plate 20 may be stamped to produce the suture apertures 24. The teeth 22 may be partially cut from the plate 20 and bent 46 in a transverse direction 11c to extend from the plate at an angle 38. The teeth 22 may be formed in any suitable geometry such as triangular, rectangular, or rectangular with a point. The width of the tooth base 30 may be selected to optimally engage a variety of tissues 14. The area from which the teeth are cut may comprise a fluid aperture 26 designed to allow the tendon 14 to receive sufficient nutrition from the synovial fluid that typically surrounds soft tissue 14.

Figure 10A:
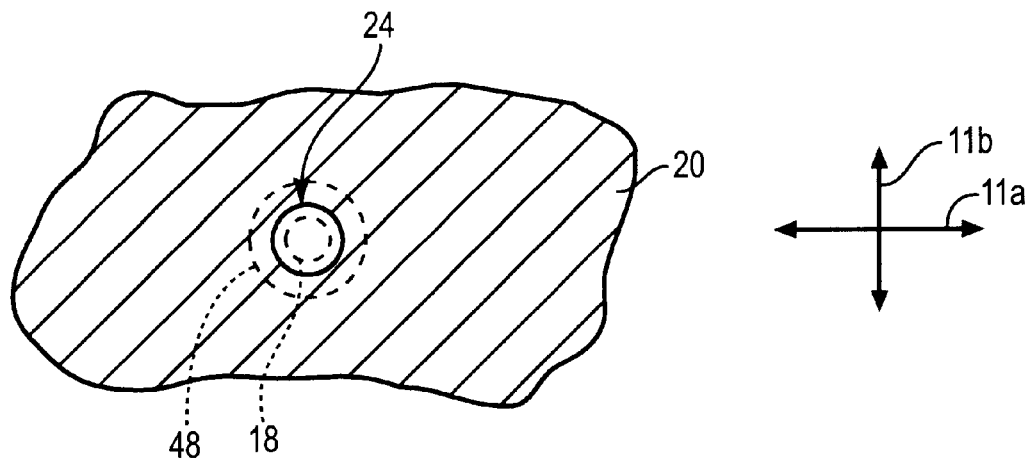
FIGS. 10a and 10b depict top and side views of an embodiment of a suture aperture capable of engaging a suture.
Figure 10B:
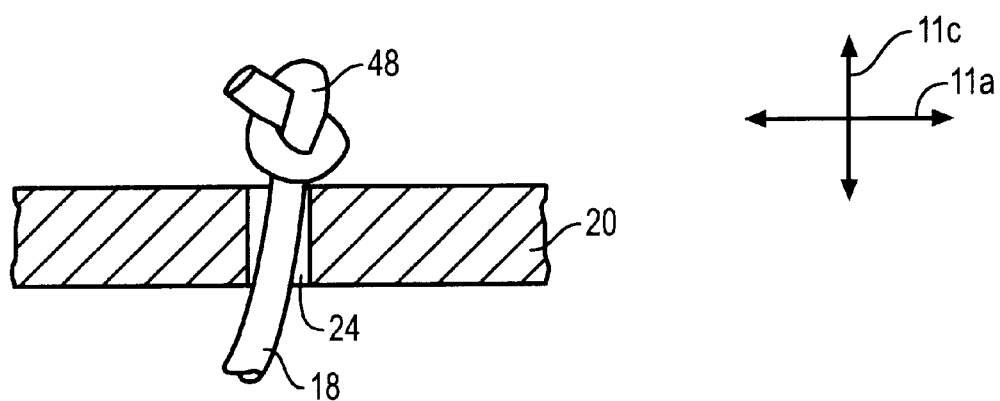

Referring to FIGS. 10a and 10b, it may be advantageous to provide a suture aperture 24 specifically configured to engage the suture 18. In certain embodiments, the suture aperture 24 may be sized only slightly larger than the suture 18 to be received therethrough. A knot may be tied in the suture 18 to create a bulbous end 48 that is too large to pass through the aperture 24 in a transverse direction 11c. The bulbous end 48 and the aperture 24 create a method for transversely securing the anchor 12 to the tendon 14. Additionally the knot method may be used to secure the anchor 12 in order to abut the tissue surface 16a against the surface 16b to enable healing of the soft tissue 14 (see FIG. 1).

Figure 11A:
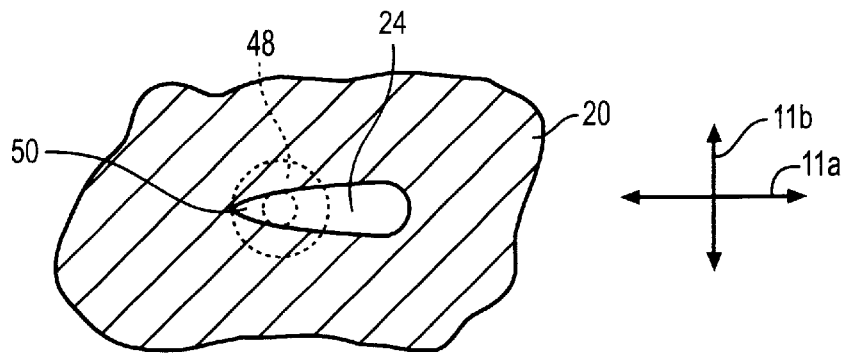
FIGS. 11a and 11b depict top and side views of an alternative embodiment of a suture aperture capable of engaging a suture.
Figure 11B:
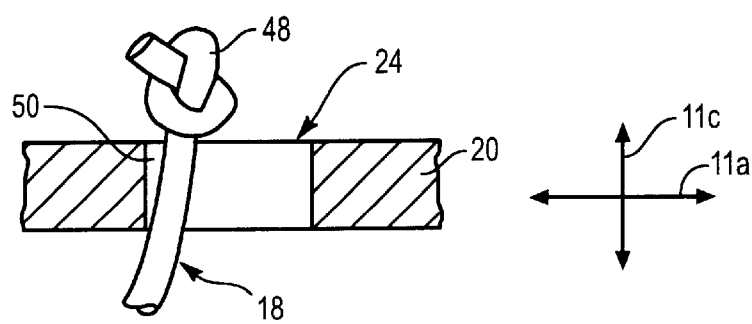

Referring to FIGS. 11a and 11b, it may be desirable to configure the suture aperture 24 to engage the body of the suture 18 to relieve the load on the bulbous end 48. The unraveling of knots in sutures and the breaking of sutures proximate knots are common modes of suture 18 failure. By relieving the load applied to a knot 48, the likelihood of knot and/or suture failure may be decreased. The suture aperture 24 may be formed with a tapered end 50. As the suture 18 is pulled tight, it typically migrates toward the tapered end 50. The walls of the tapered end 50 may pinch the suture 18, thereby supporting a portion of the load.

Figure 12A:
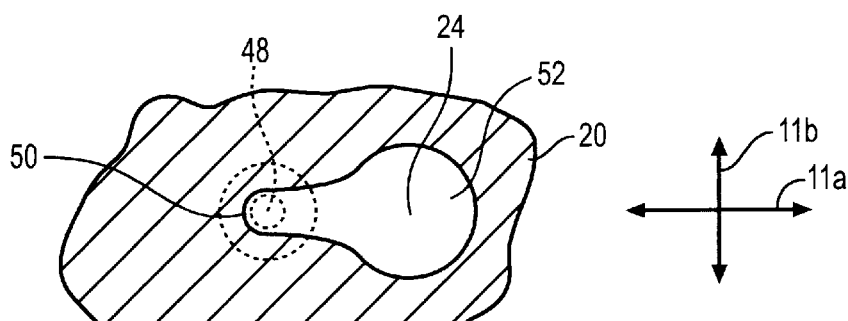
FIGS. 12a and 12b depict top and side views of an alternative embodiment of a suture aperture capable of engaging a suture.
Figure 12B:
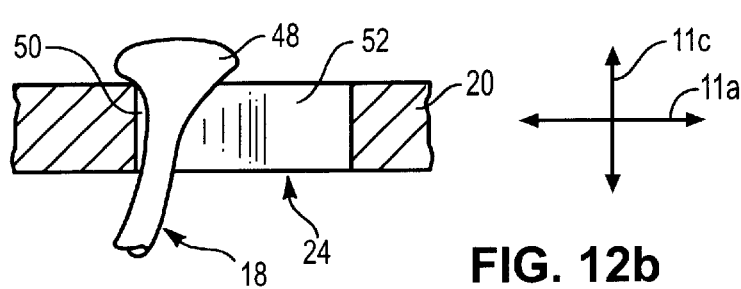

Referring to FIGS. 12a and 12b, in selected embodiments in accordance with the present invention, a suture 18 may be formed with a pre-made bulbous end 48. Such a pre-made bulbous end 48 eliminates the problems associated with the unraveling of knots in sutures. The suture aperture 24 may be formed as a single circular hole 24 sized to prevent the pre-made bulbous end 48 from passing therethrough, as discussed hereinabove. Alternatively, the aperture 24 may be formed with an open end 52 of sufficient size to allow the bulbous end 48 to pass therethrough, and a tapered end 50 sized to prevent passage of the bulbous end 48.

Referring to FIGS. 13a and 13b, a multitude of suture 18 configurations exist that may used in accordance with the present invention. FIGS. 13a and 13b illustrate a top view 42 and a side view 36 of a selected embodiment of a repair 10. A first anchor 12a may engage a first tendon 14a. A second anchor 12b may engage a second tendon 14b. In the depicted embodiment, a longitudinal securement mechanism 18a comprises a first suture 18a securing the first anchor 12a to the second anchor 12b. In the depicted embodiment, the first suture 18a passes through the repair site 16. A second suture 18b transversely secures the first anchor 12a to the first tendon 14a and a third suture 18c transversely secures the second anchor 12b to the second tendon 14b.

The transverse securement 18b, 18c prevents the anchors 12 from disengaging the tendon 14. The longitudinal securement 18a supports the tensile loads associated with mobilization of the tendon 14, thus preventing separation of the repair site 16. Stitches 54 may be added to maintain the proper alignment of the repair site 16.

Referring to FIGS. 14a and 14b, a first anchor 12a may engage a first tendon 14a. A second anchor 12b may engage a second tendon 14b. A longitudinal securement 18 comprises a suture 18 securing the first anchor 12a to the second anchor 12b. The suture 18 may pass through the repair site 16. Additionally, the suture 18 transversely secures the first anchor 12a to the first tendon 14a and the second anchor 12b to the second tendon 14b.

Figure 15A:
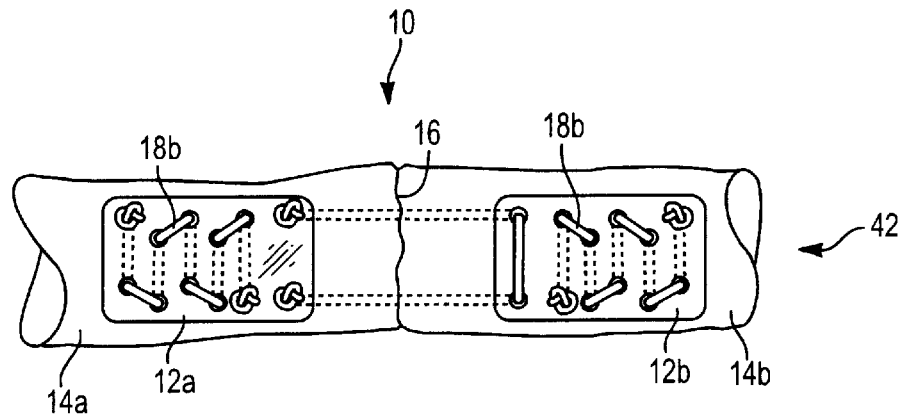
FIGS. 15a and 15b depict top and side views of an alternative embodiment of a repair in accordance with the present invention.
Figure 15B:
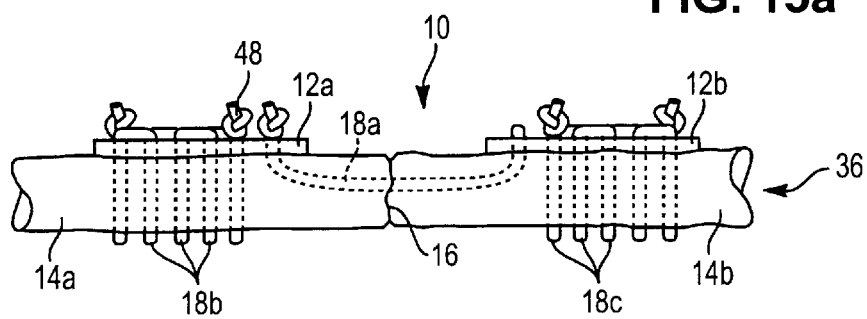

Referring to FIGS. 15a and 15b, in selected embodiments, the anchors 12 may be configured to engage the tendon 14 without the use of penetrating teeth 22. FIG. 15 illustrates a top view 42 and a side view 36 of a repair 10 wherein sutures 18b, 18c provide both securement in both a longitudinal direction 11a and a transverse direction 11c, thus eliminating the need for teeth 22. A first anchor 12a may engage a first tendon 14a. A second anchor 12b may engage a second tendon 14b. A longitudinal securement 18a, comprising a first suture 18a, secures the first anchor 12a to the second anchor 12b. The first suture 18a may pass through the repair site 16.

A second suture 18b may make several passes through the tendon 14. The number of passes may be selected to provide the necessary resistance to motion in a longitudinal direction 11a between the anchor and the tendon 14. A third suture 18c may be applied similar to the second suture 18b to secure the second anchor 12b to the second tendon 14b in both a longitudinal direction 11a and a transverse direction 11c. The sutures 18b, 18c may pass through the tendon 14 in a manner so as to create the weaving pattern discussed hereinabove.

Figure 16A:
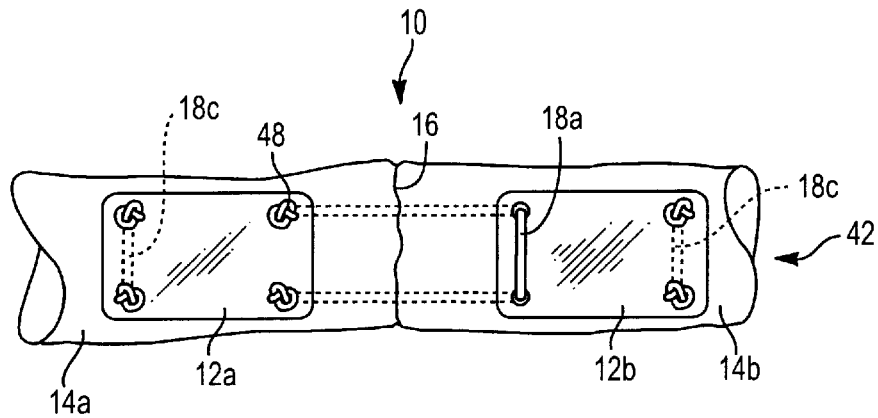
FIGS. 16a and 16b depict top and side views of an alternative embodiment of a repair in accordance with the present invention.
Figure 16B:
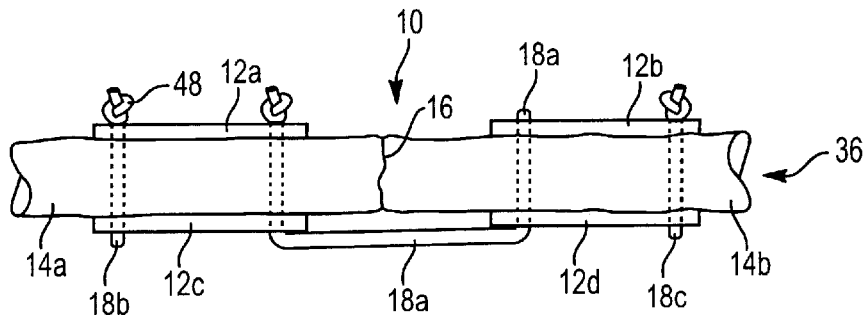

Referring to FIGS. 16a and 16b, in selected embodiments, two anchors 12 may be configured to engage each of the first tendon 14a and second tendons 14a, 14b. A first anchor 12a may engage the top surface of the first tendon 14a. A second anchor 12b may engage the top surface of the second tendon 14b. A third anchor 12c may engage the bottom surface of the first tendon 14a. A fourth anchor 12d may engage the bottom surface of the second tendon 14b. A longitudinal securement 18a, comprising a first suture 18a, secures the first anchor 12a to the third anchor 12c, the third anchor 12c to the fourth anchor 12d, and the fourth anchor 12d to the second anchor 12b. In this configuration, the first suture 18a may avoid passing through the repair site 16. A second suture 18b may transversely secure the first anchor 12a to the third anchor 12c. A third suture 18c may transversely secure the second anchor 12b to the fourth anchor 12d.

Figure 17A:
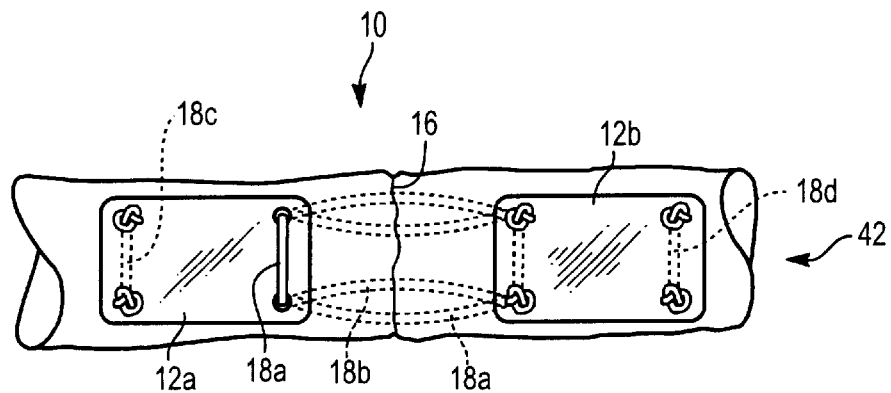
FIGS. 17a and 17b depict top and side views of an alternative embodiment of a repair in accordance with the present invention.
Figure 17B:
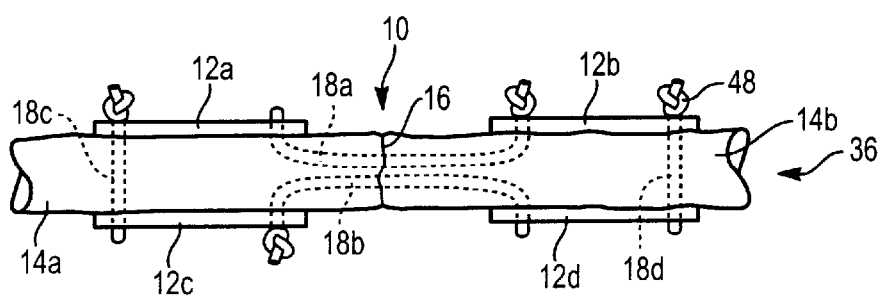

Referring to FIGS. 17a and 17b, a first anchor 12a may engage the top surface of the first tendon 14a. A second anchor 12b may engage the top surface of the second tendon 14b. A third anchor 12c may engage the bottom surface of the first tendon 14a. A fourth anchor 12d may engage the bottom surface of the second tendon 14b. A first suture 18a may longitudinally secure the first anchor 12a to the second anchor 12b. A second suture 18b may longitudinally secure the third anchor 12c to the fourth anchor 12d. A third suture 18c may transversely secure the first anchor 12a to the third anchor 12c. A fourth suture 18d may transversely secure the second anchor 12b to the fourth anchor 12d. In such a configuration, four suture strands 18a, 18b support the load in a longitudinal direction 11a associated with mobilization.

Figure 18A:
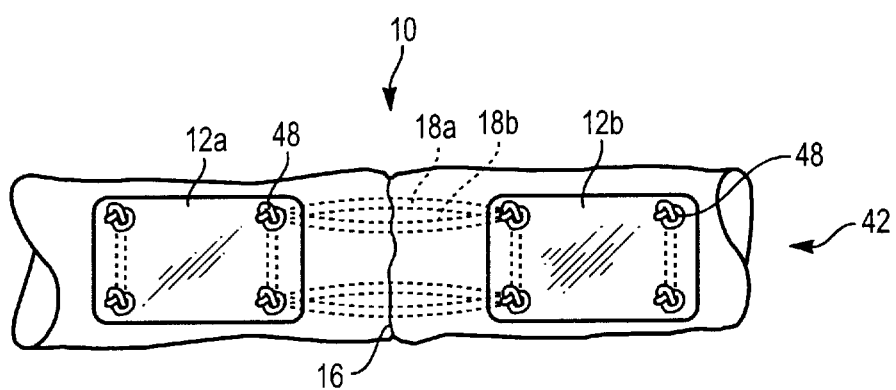
FIGS. 18a and 18b depict top and side views of an alternative embodiment of a repair in accordance with the present invention.
Figure 18B:
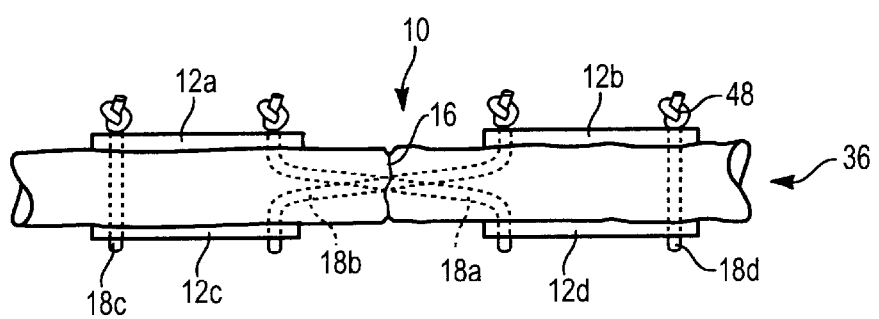

Referring to FIGS. 18a and 18b, a first anchor 12a may engage the top surface of the first tendon 14a. A second anchor 12b may engage the top surface of the second tendon 14b. A third anchor 12c may engage the bottom surface of the first tendon 14a. A fourth anchor 12d may engage the bottom surface of the second tendon 14b. A first suture 18a may longitudinally secure the first anchor 12a to the fourth anchor 12d. A second suture 18b may longitudinally secure the second anchor 12b to the third anchor 12c. A third suture 18c may transversely secure the first anchor 12a to the third anchor 12c. A fourth suture 18d may transversely secure the second anchor 12b to the fourth anchor 12d.

Figure 19A:
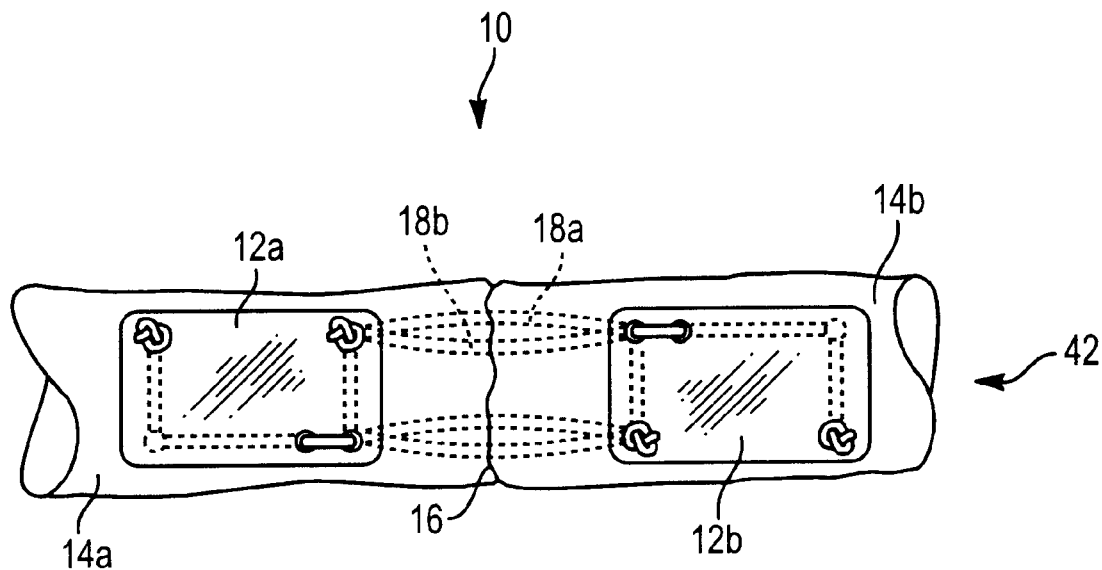
FIGS. 19a and 19b depict top and side views of an alternative embodiment of a repair in accordance with the present invention.
Figure 19B:
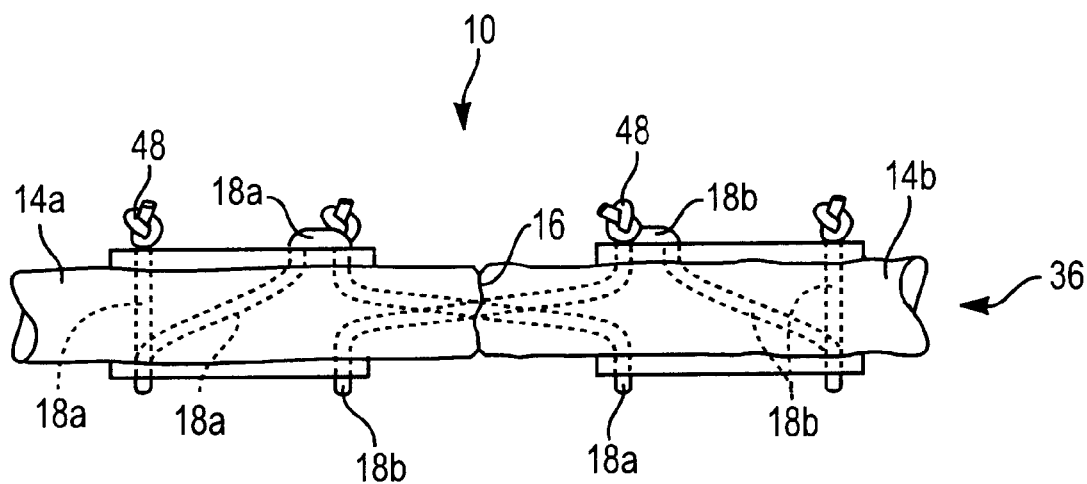

Referring to FIGS. 19a and 19b, a first anchor 12a may engage the top surface of the first tendon 14a. A second anchor 12b may engage the top surface of the second tendon 14b. A third anchor 12c may engage the bottom surface of the first tendon 14a. A fourth anchor 12d may engage the bottom surface of the second tendon 14b. A first suture 18a longitudinally secures the first anchor 12a to the fourth anchor 12d. The first suture 18a may also transversely secure the first anchor 12a to the third anchor 12c. A second suture 18b longitudinally secures the second anchor 12b to the third anchor 12c. The second suture 18b may also transversely secure the second anchor 12b to the fourth anchor 12d.

Figure 20:
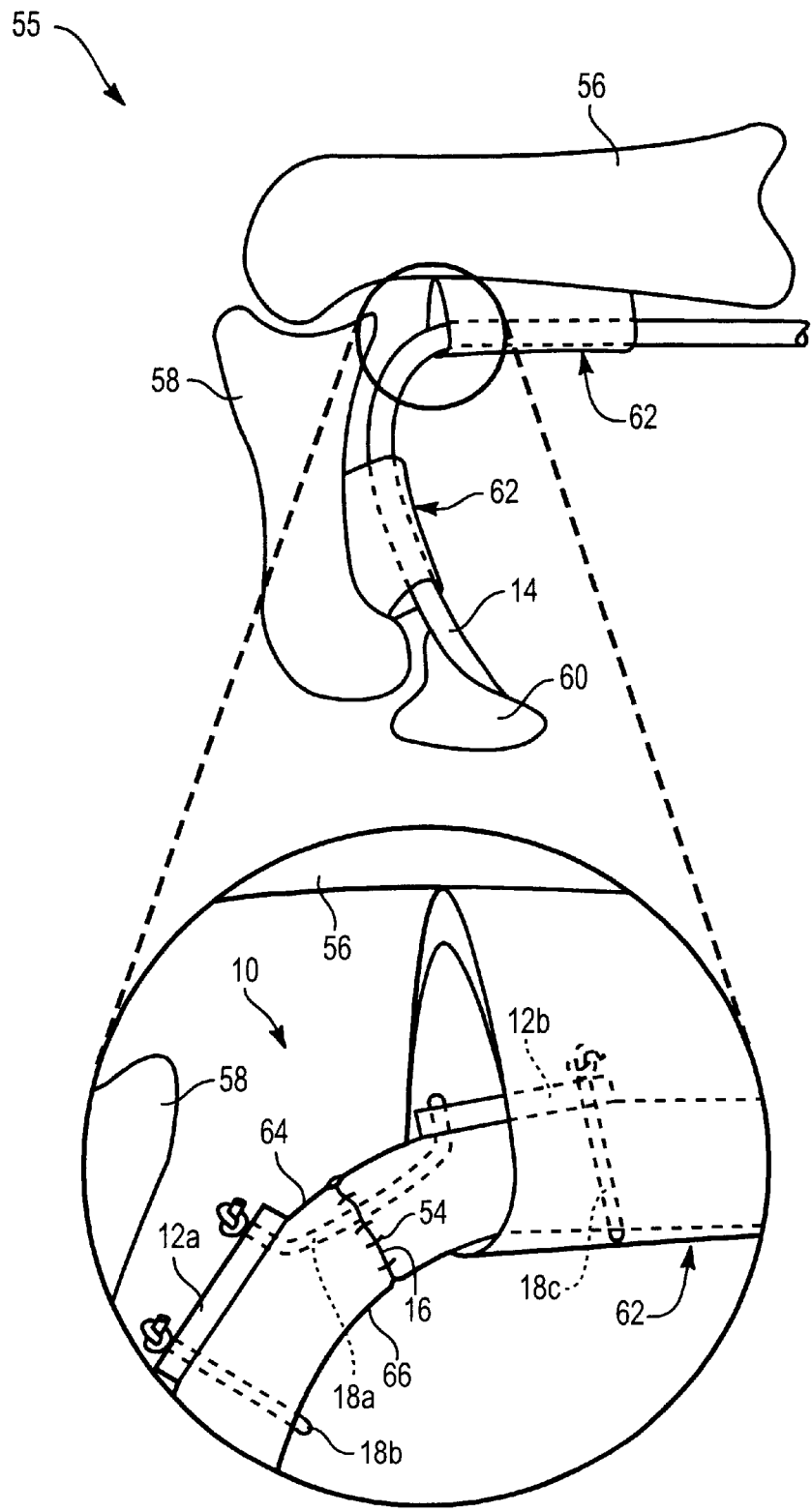
FIG. 20 is a side view of a repair of a severed flexor profundus tendon in accordance with the present invention.

FIG. 20 is a side view of a repair of a severed flexor profundus tendon 14 of a finger 55 in accordance with the present invention. The bones of finger 55 comprise first row, second row, and third row phalanges 56, 58, and 60. The first row and second row phalanges 56, 58 each have a synovial sheath 62 secured thereto. The sheath 62 creates a system of pulleys on which the tendon 14 may glide. The flexor profundus tendon 14 secures to the third row phalange 60. When the tendon 14 is tensioned by muscles in the hand and forearm, the finger 55 flexes or curls.

The dorsal fibers 64 of tendons 14 are often exposed to greater tensile loads than are the palmar fibers 66. As a result, the dorsal fibers 64 are often the strongest. In certain embodiments, it may be advantageous to position the tensile (longitudinal) supports 18a in the region of the dorsal fibers 64. In selected embodiments, the anchors 12 may be secured to the dorsal side of the tendons 14. Such a configuration may facilitate the reinforcement the of the dorsal fibers 64. Additionally, as the tendon 14 is tensioned, it is pulled against the palmar surface of the synovial sheath 62. The dorsal securement of the anchors 12 permits the tendon 14 to glide unobstructed and smoothly along the sheath 62. In certain embodiments, however, the anchors 12 may have a sufficiently low profile to allow for palmar securement of the anchors 12 without significantly inhibiting glide of a tendon 14 through the sheath 62.

Figure 21:
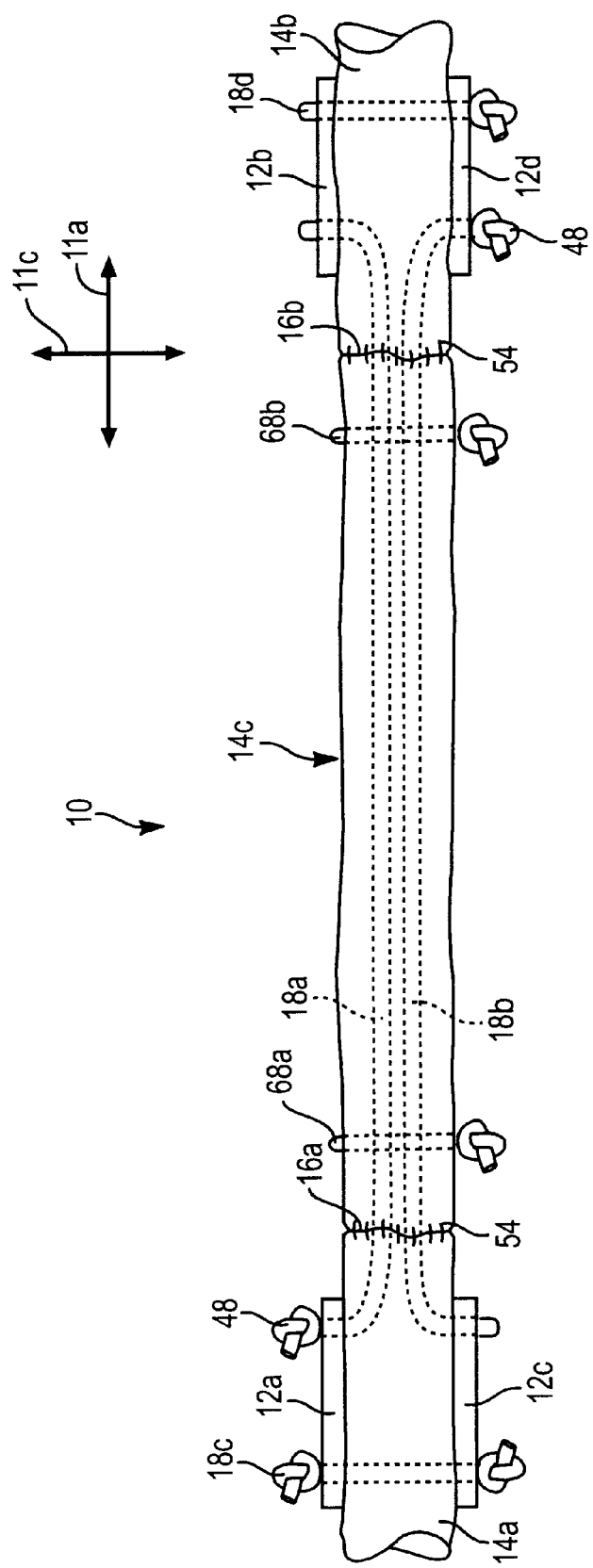
FIG. 21 is a side view of a tendon graft in accordance with the present invention.

Referring to FIG. 21, selected embodiments in accordance with the present invention may provide efficient tendon 14 grafting. A graft tendon 14c having a first and second end may be inserted between the first and second tendon 14a, 14b, the first end forming a first repair site 16a with the first tendon 14a and the second end forming a second repair site 16b with the second tendon 14b. Any suitable anchoring configuration in accordance with the present invention, as previously described, may be employed to secure the graft. In one presently preferred embodiment, a first anchor 12a may engage the top surface of the first tendon 14a. A second anchor 12b may engage the top surface of the second tendon 14b. A third anchor 12c may engage the bottom surface of the first tendon 14a. A fourth anchor 12d may engage the bottom surface of the second tendon 14b.

A first suture 18a may secure to the first anchor 12a, pass through the graft tendon 14c, and secure to the second anchor 12b. A second suture 18b may secure to the third anchor 12c, pass through the graft tendon 14c, and secure to the fourth anchor 12d. A third suture 18c may transversely secure the first anchor 12a to the third anchor 12c. A fourth suture 18d may transversely secure the second anchor 12b to the fourth anchor 12d. Tie sutures 68 may be applied to the first and second ends of the graft tendon 14c to mitigate the risk of separation at the repair site 16.

Figure 22:
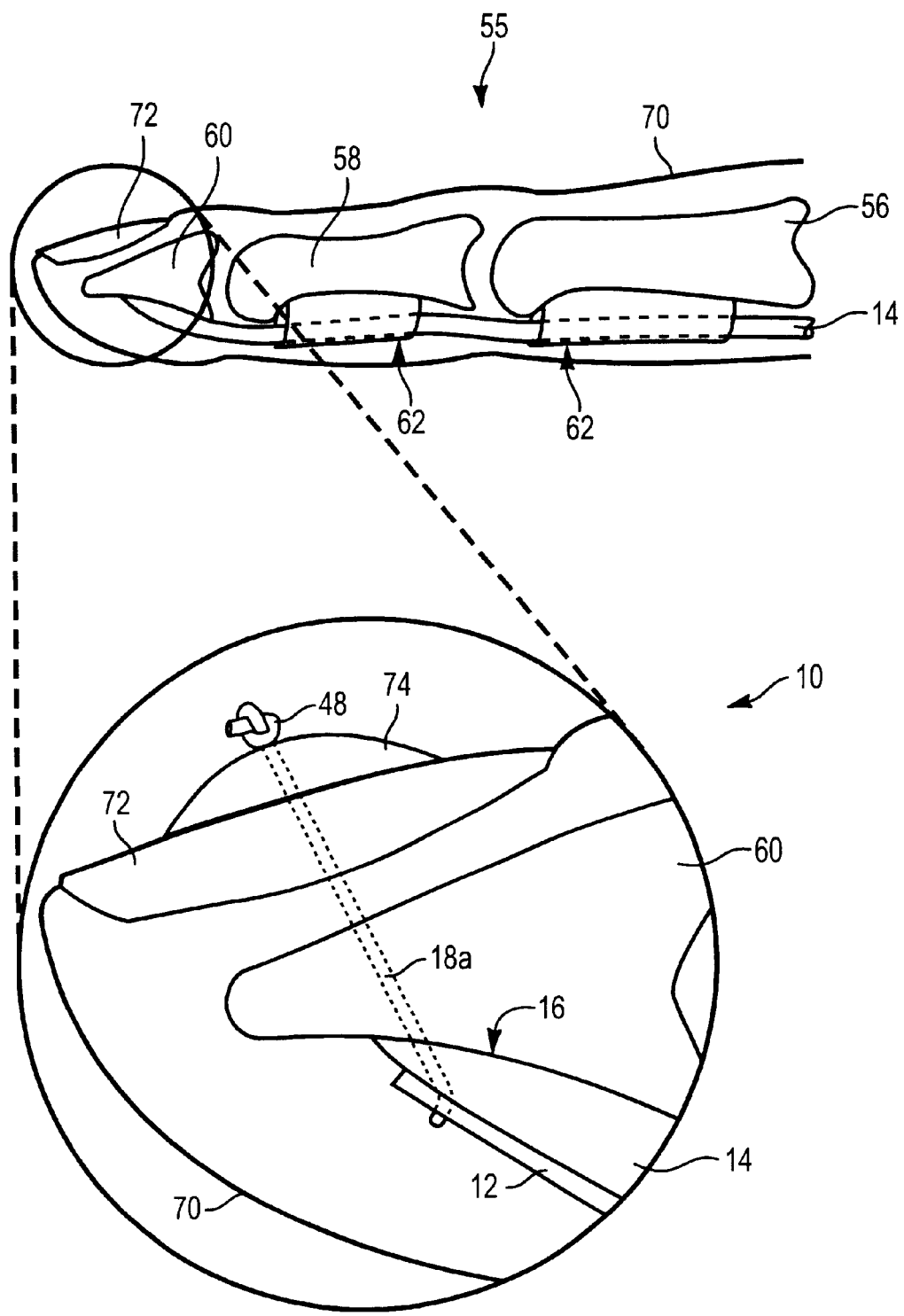
FIG. 22 is a side view of a repair of a ruptured flexor profundus tendon in accordance with the present invention.

Referring to FIG. 22, in certain embodiments, it may be necessary to secure a soft tissue 14 against a dissimilar material. For example, it may be necessary to secure a flexor profundus tendon 14 to the third row phalange 60. FIG. 22 illustrates a finger 55 with skin 70 and fingernail 72. An anchor 12 may engage the ruptured tendon 14. A suture 18 may secure to the anchor 12 and extend through the finger tip and exit through the fingernail 72. A stop 74 may be placed over the fingernail 72 to prevent the suture 18 and bulbous end 48 from loosening.

The present invention may be embodied in other specific forms without departing from its structures, methods, or other essential characteristics as broadly described herein. The described embodiments are to be considered in all respects only as illustrative, and not restrictive.

From the above discussion, it will be appreciated that the present invention provides novel apparatus and methods for engaging, securing, and abutting soft tissue against an opposing surface to enable the tissue to heal and to join the soft tissue with the opposing surface. The present invention may be particularly useful in securing soft tissue that may be loaded and in tension during the healing process. The apparatus and methods in accordance with the present invention may support tensile loads, thus allowing the tissue to heal while also permitting mobilization of the healing tissue. Selected tissues have been found to heal with a better final result when such tissues are mobilized early in the healing process and/or continue to be mobilized throughout the healing process. The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by United States Letters Patent is:

1. A pair for soft tissue defining longitudinal, lateral, and transverse directions substantially orthogonal to one another and having a severed face, the repair comprising:
   a first anchor contacting the soft tissue proximate the severed face;
   a first suture securing the anchor to the soft tissue in the transverse direction;
   a second suture engaging the anchor and securing the severed face of the soft tissue in abutment against a selected surface; and
   the first anchor comprising a plate paving teeth extending generally transversely therefrom to penetrate the soft tissue and resist motion in substantially the longitudinal and lateral directions between the first anchor and the soft tissue, the teeth having barbs engaging a the fibers of the soft tissue to substantially restrict transverse motion between the first anchor and the soft tissue after penetration of the teeth into the soft tissue.

2. The repair of claim 1, wherein the plate includes a plurality of apertures formed therein.

3. The repair of claim 2, wherein the teeth are staggered in a lateral direction to engage the fibers of the soft tissue in a weaving pattern.

4. The repair of claim 3, wherein the first and second sutures comprise a single suture.

5. The repair of claim 3, wherein the first anchor comprises a material selected from the group consisting of surgical steel, titanium, a metal alloy, a bio-absorbable material, a polymer, and a reinforced polymer.

6. The repair of claim 5, wherein selected apertures of the plurality of apertures comprise suture apertures for receiving the first and second sutures therethrough.

7. The repair of claim 6 wherein at least one of the suture apertures restricts transverse motion of a suture of the first and second sutures therethrough.

8. The repair of claim 7, wherein a suture of the first and second sutures has a bulbous end restricting transverse motion thereof through the suture apertures.

9. The repair of claim 8, wherein the soft tissue comprises a first tendon and the severed face constitutes a cross-section of the first tendon.

10. The repair of claim 9, wherein the selected surface comprises a severed cross-sectional surface of a second tendon.

11. The repair of claim 10, further comprising a second anchor engaging the second tendon proximate the severed cross-sectional surface.

12. The repair of claim 11, wherein the second suture engages the first anchor and the second anchor to maintain the severed face of the first tendon in abutment against the severed cross-sectional surface of the second tendon.

13. The repair of claim 12, further operably attached to a graft tendon having a first end and a second end, wherein the second suture secures the first anchor to the second anchor and maintains the severed face of the first tendon against the first end of the graft tendon and the severed cross-sectional surface of the second tendon against the second end of the graft tendon.

14. The repair of claim 1, wherein the first anchor includes a plurality of apertures, wherein selected apertures of the plurality of apertures are formed as suture apertures to admit a suture of the first and second sutures and other selected apertures of the plurality of apertures allow nutrient fluids to contact the soft tissue below the first anchor.

15. The repair of claim 1, wherein the first anchor is made of a material selected from the group consisting of surgical steel, titanium, a metal alloy, a bio-absorbable material, a polymer, and a reinforced polymer.

16. The repair of claim 1, wherein the first anchor has a plurality of apertures, wherein selected apertures of the plurality of apertures are formed as suture apertures to resist motion, in the transverse direction, of the suture therethrough.

17. The repair of claim 1, wherein the soft tissue is a first tendon and the selected surface is the severed cross-sectional surface of a second tendon.

18. The repair of claim 1, wherein the soft tissue and the selected surface are dissimilar materials.

19. A method for repairing soft tissue defining longitudinal, lateral, and transverse directions substantially orthogonal to one another and having a severed face, the method comprising:

providing an anchor comprising a plate having teeth extending generally transversely therefrom to penetrate the soft tissue and resist motion in substantially the longitudinal and lateral directions between the first anchor and the soft tissue;

applying the anchor to the soft tissue proximate the severed face;

securing the anchor to the soft tissue in the transverse direction with a first suture; and engaging the anchor with a second suture; and manipulating the second suture to maintain the severed face in abutment against a selected surface.

20. An implant having longitudinal, lateral, and transverse directions substantially orthogonal to one another, the implant comprising:

a plate extending substantially exclusively in a plane defined by the longitudinal and lateral directions to form the edges of the implant;

the plate having a plurality of apertures extending in the transverse direction therethrough, selected apertures of the plurality of apertures being formed to receive sutures; and a plurality of teeth extending generally transversely from the plate.

* * * * *